US010166393B2

(12) United States Patent
Bonnet et al.

(10) Patent No.: US 10,166,393 B2
(45) Date of Patent: Jan. 1, 2019

(54) ACTIVE IMPLANTABLE MEDICAL DEVICE FOR HEART FAILURE TREATMENT BY STIMULATION OF THE VAGUS NERVE

(71) Applicants: SORIN CRM SAS, Clamart (FR); UNIVERSITÉ DE RENNES 1, Rennes (FR)

(72) Inventors: Jean-Luc Bonnet, Massy (FR); Mélanie Mullemeester, Montrouge (FR); Alfredo Hernandez, Cesson-Sévigné (FR); Guy Carrault, Cesson-Sévigné (FR)

(73) Assignees: SORIN CRM SAS, Clamart (FR); UNIVERSITÉ DE RENNES 1, Reenes (FR)

( * ) Notice: Subject to any disclaimer, the term of this patent is extended or adjusted under 35 U.S.C. 154(b) by 496 days.

(21) Appl. No.: 14/883,378

(22) Filed: Oct. 14, 2015

(65) Prior Publication Data

US 2016/0136428 A1    May 19, 2016

(30) Foreign Application Priority Data

Oct. 16, 2014    (FR) ...................................... 14 59919

(51) Int. Cl.
*A61N 1/00*    (2006.01)
*A61N 1/36*    (2006.01)
*A61N 1/362*    (2006.01)

(52) U.S. Cl.
CPC ..... *A61N 1/36139* (2013.01); *A61N 1/36053* (2013.01); *A61N 1/36114* (2013.01); *A61N 1/36135* (2013.01); *A61N 1/3627* (2013.01)

(58) Field of Classification Search
CPC ............ A61N 1/36139; A61N 1/36053; A61N 1/36114; A61N 1/36135; A61N 1/3627
See application file for complete search history.

(56) References Cited

U.S. PATENT DOCUMENTS

| 8,433,419 | B2 | 4/2013 | Chavan et al. |
| 2005/0256545 | A1* | 11/2005 | Koh ...................... A61B 5/0031 607/17 |
| 2005/0267542 | A1* | 12/2005 | David .................... A61B 5/412 607/17 |
| 2012/0095530 | A1 | 4/2012 | Chavan et al. |
| 2012/0172742 | A1 | 6/2012 | Arcot-Krishnamurthy et al. |

FOREIGN PATENT DOCUMENTS

| EP | 0 657 187 | 6/1995 |
| WO | WO-2014/074523 | 5/2014 |

OTHER PUBLICATIONS

Preliminary Search Report for French Patent Application No. 1459919, dated Jun. 3, 2015, 2 pages.

* cited by examiner

*Primary Examiner* — Lindsey G Wehrheim (74) *Attorney, Agent, or Firm* — Foley & Lardner LLP (57) ABSTRACT

The invention relates to an active implantable medical device. The device includes a VNS pulse generator, an activity sensor for detecting a patient's current activity level, and a processor. The processor is configured to collect the electrical activity of the heart, such as a current intrinsic heart rate of the patient. The processor further calculates values of a reference heart rate based on the patient's current activity level. A first histogram is constructed from the reference heart rate values, and a second histogram is constructed from the intrinsic heart rate values. An index representative of the patient's condition is derived by comparing the first and second histograms.

17 Claims, 7 Drawing Sheets

ACTIVE IMPLANTABLE MEDICAL DEVICE FOR HEART FAILURE TREATMENT BY STIMULATION OF THE VAGUS NERVE

CROSS-REFERENCE TO RELATED PATENT APPLICATIONS

This application claims the benefit of and priority to French Patent Application No. 1459919, filed Oct. 16, 2014, which is incorporated herein by reference in its entirety.

BACKGROUND

The invention relates to "active implantable medical devices" as defined by the Directive 90/385/EEC of 20 Jun. 1990 of the Council of the European Communities, namely implants for delivering stimulation therapy to the vagus nerve or to one of its branches, known as VNS (Vagus Nerve Stimulation) therapy.

It more particularly relates to the use of such therapies in patients at risk of heart failure.

VNS acts on cardiovascular function by reducing heart rate and myocardial contractility with decreased duration of diastole, which may help reduce the development of cardiac remodeling that may lead to heart failure.

In general, patients with risk of heart failure have an increased heart rate (HR) compared to healthy patients, which may require taking drugs such as beta blockers to reduce the heart rate and thus improve the patient prognosis.

A high heart rate is often a predictor of increased mortality in the general population, with a higher risk of stroke, this risk being typically increased by 3% for each increase of one beat per minute (bpm) of the average heart rate.

It is also known that VNS therapies have a direct effect on heart rate by acting on the parasympathetic balance. This heart rate reduction effect occurs:

In the short term, by a change in the SympathoVagal Balance (SVB) leading to a restoration of a heart rate well suited to the patient's current activity, and In the long term with beneficial effects after months of VNS therapy even if the instant restoration of SVB balance is not reached.

One of the difficulties of VNS therapy lies in the adjustment of the stimulation parameters.

In the short term, when dynamic change of the stimulation, depending on the patient's instantaneous activity, is required, this change is made from a variety of parameters representative of the patient's current condition such as heart rate, metabolic needs, etc.

VNS therapy is then automatically controlled or modulated as a function of the level of detected current activity, for example by selection between a plurality of energy levels of VNS stimulation pulses.

However, when adjustment of the VNS therapy parameters is desirable for getting a beneficial effect in the long term, this adjustment is generally left to the discretion of the physician, who does it more or less empirically.

Furthermore, adjustment or readjustment of these parameters by the physician is only performed during monitoring visits, even though the patient's condition can change over time, due to VNS therapy or independently thereof, and the initial setup does not reflect these changes.

Thus, techniques such as those described for example by US 2012/0095530 A1 (U.S. Pat. No. 8,433,419 B2) are used to adapt the VNS therapy to the patient's activity level. The activity level can be evaluated by an appropriate sensor such as an accelerometer integrated into the housing of the implanted VNS pulse generator. The sensor signal is compared to a set of predefined thresholds, and the VNS stimulation parameters, mainly the stimulation energy, are selectively adjusted according to the crossed thresholds, especially to adapt the therapy by allowing the expression of an increased heart rate correlated to the effort.

However, with this device the modulation of VNS therapy does not take into account the medium and/or long-term evolution (e.g. one day to another and/or over a period of several days or weeks) of the pathology of the patient, in case of worsening as well as in case of improving of his/her condition.

Other similar techniques have been proposed, but it is always to make a dynamic adaptation of the VNS therapy by rate response over a signal from an activity sensor or other sensor of a physiological parameter of the patient. This dynamically improves the instant effectiveness of the VNS therapy but without taking into account changes in the long term of the patient's condition.

WO 2014/074523 A1 discloses a VNS stimulator for storing various physiological and stimulation data, and incorporating adaptation functions in the time of VNS stimulation, controlled for example by monitoring arrhythmias induced by therapy, or implementing a weighting of physiological events stored so as to give greater importance to recent events compared to the oldest ones.

SUMMARY

According to one embodiment of the invention, a technique is provided to automatically adapt the parameters of a VNS therapy based on a patient's physiological activity monitored over a given period of time. A retrospective analysis over the long term of patient activity, for example over a period of one month, is performed. A comparison between an intrinsic patient heart rate ($HR_{int}$), measured by the device, and a reference heart rate ($HR_{ref}$), calculated according to the aforementioned retrospective analysis, is performed based on data produced by an activity sensor.

The intrinsic heart rate $HR_{int}$ may be determined from the measured inter-beat (RR) intervals, excluding all pathological cycles (especially those containing extrasystoles), those having noise, those with over-detection or under-detection, etc.

For a normal patient, the values of the reference rate $HR_{ref}$ calculated from the activity sensor are very close to those of the intrinsic rhythm $HR_{int}$.

In contrast, in the case of pathology, particularly for patients at risk of heart failure, the intrinsic rhythm $HR_{int}$ will exceed the reference rhythm $HR_{ref}$.

However, if the patient's general condition is improving, it is assumed that:

the reference rhythm $HR_{ref}$ increases due to better physical activity, and simultaneously the intrinsic rhythm $HR_{int}$ decreases due to the improvement of the patient's condition relative to its pathology, in part due to the issuance of VNS therapy.

Therefore, the two values $HR_{int}$ and $HR_{ref}$ will tend to converge, leading to a diagnosis of an improved patient condition.

Conversely, if the gap increases, alerts can be generated so that the physician following the patient can be warned without waiting for the next visit.

Also, the parameters of the VNS stimulation may be modified according to the diagnosis of improvement or worsening of the patient's condition.

Specifically, one exemplary embodiment of the invention provides an active implantable medical device for the treatment of heart failure by VNS stimulation, including in a manner in itself known, notably from the WO 2014/074523 A1 above: a VNS pulse generator and an electrode able to be placed on the vagus nerve or proximity thereof; an activity sensor, capable of delivering successive values of the patient's current level of activity; methods for collecting the electrical activity of the heart, capable of delivering successive values of the patient's current intrinsic heart rate $HR_{int}$; and methods for calculating a reference heart rate, able to calculate successive values of the reference heart rate according to the respective values of the patient's current activity level.

Various embodiments of the invention further include:

methods for construction of a first histogram from said reference heart rate values $HR_{ref}$ calculated depending on the respective values of the patient's current activity level issued by the activity sensor, over a predetermined monitoring period;

methods for construction of a second histogram, separate from the first histogram, from said intrinsic heart rate values $HR_{int}$ based on the electrical activity of the heart over said monitoring period; and comparison methods adapted to compare the first and second histogram and to derive an index representative of the patient's condition at the end of the monitoring period.

According to various advantageous subsidiary characteristics:

the comparison methods are adapted to calculate, for each of the first and second histograms, at least one parameter of the histogram, and to compare said respective parameter(s) for deriving said index representative of the patient's condition at the end of the monitoring period;

the histogram parameter belongs to the group including: maximum value of the histogram, histogram of average value, median of the histogram values, area under the histogram envelope curve, and combinations thereof;

the methods of calculation of the reference heart rate are methods adapted to apply the following relationship:

$$Fg = \text{Basic\_rate} + (\text{G\_sample} + \text{G\_low\_point})\frac{\text{Max\_rate} - \text{Basic\_rate}}{\text{G\_high\_point} - \text{G\_low\_point}}$$

Fg being the value of the reference heart rate, G_sample being the value of the patient's current activity level issued by the activity sensor, and Basic_rate, max_rate, G_high_point and G_low_point being predetermined constants;

the methods of calculation of the reference heart rate are methods adapted to further operate a filtering of the calculated reference heart rate value, by applying a time constant to the heart rate reference values successively calculated;

the device further comprises control means such as a controller or computer processor programmed to evaluate the changes in said index representative of the patient's condition over a plurality of successive monitoring periods;

the control means may be further adapted to modify at least one operating parameter of the VNS generator according to the verification or not of predetermined criteria by said variations in said index representative of the patient's condition over said plurality of successive monitoring periods;

the control means may be further adapted to trigger an alert depending on the verification or not of predetermined criteria by said variations in said index representative of the patient's condition over said plurality of successive monitoring periods.

BRIEF DESCRIPTION OF THE DRAWINGS

Further features, characteristics and advantages of the present invention will become apparent to a person of ordinary skill in the art from the following detailed description of preferred embodiments of the present invention, made with reference to the attached drawings, in which like reference characters refer to like elements and in which.

DETAILED DESCRIPTION

An exemplary embodiment of the technique of the invention will now be described.

Regarding its software aspects, the invention may be implemented by appropriate programming of the controlling software of a known stimulator of the vagus nerve (VNS stimulator).

Such a pacemaker includes a programmable microprocessor provided with circuits for shaping and delivering stimulation pulses to implanted electrodes. It is possible to transmit to it by telemetry software that will be stored in memory and executed to implement the functions of the invention which will be described below. The adaptation of these devices to implement the functions of the invention is within the reach of a person skilled in the art and will not be described in detail.

The method of the invention is implemented primarily by software, through appropriate algorithms performed by a microcontroller or a digital signal processor. For the sake of clarity, the various processing applied will be decomposed and schematized by a number of separate functional blocks in the form of interconnected circuits, but this representation, however, is only illustrative, these circuits including common elements in practice corresponding to a plurality of functions generally performed by the same software.

Figure 1:
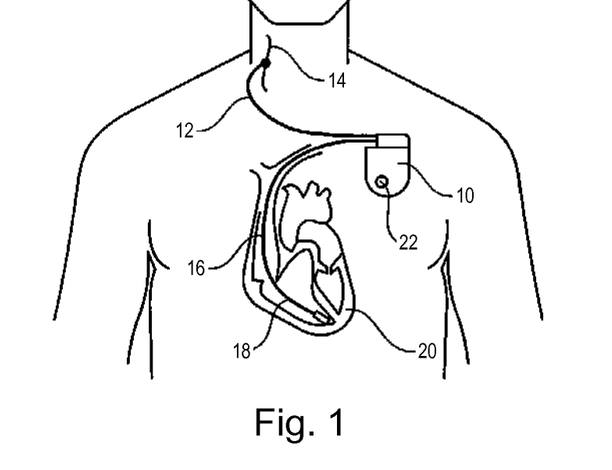
FIG. 1 is an overview presentation of the device of the invention, showing the pulse generator, the heart and the cervical vagus nerve as well as the leads used.

In FIG. 1, reference 10 designates the housing of a pulse generator. The vagus nerve stimulation is delivered by a lead 12 carrying at its distal end an electrode implanted in the cervical vagus nerve 14 and able to stimulate the latter by applying pulse trains produced by the generator 10. This technique of stimulation of the parasympathetic system is nevertheless not limiting and other methods may be used for this purpose.

The generator 10 is also provided with a cardiac lead 16. The cardiac lead is provided at its distal end 18 an electrode for collecting of the electrical activity of the heart 20. The lead 16 collects the endocardial electrogram signals (EGM) that will deliver a signal representative of the patient's cardiac activity, in the present case the heart rate, determined by the duration of RR intervals of successive cardiac depolarizations. This technique of collection of heartbeat is however not exhaustive and other methods can be employed for this purpose.

The housing 10 is also provided with an activity sensor 22, including a motion sensor such as an accelerometer or "G sensor". Again, this particular type of sensor is not limiting, and other collection methods of patient activity parameter can be used, for example a physiological sensor such as a minute ventilation (MV) sensor giving indication of the patient's activity level according to his/her metabolic requirements measured from the respiratory rate and tidal volume.

Figure 2:
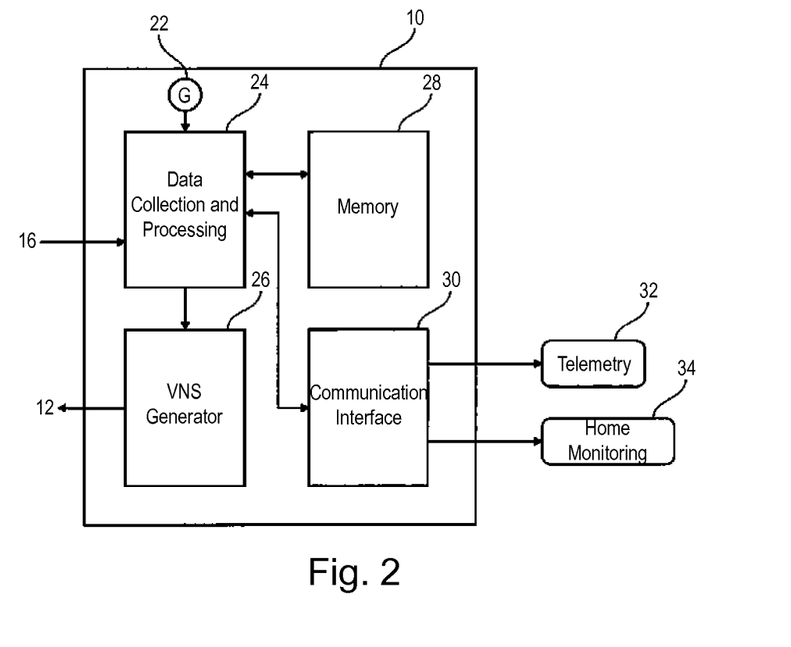
FIG. 2 is a block diagram illustrating the main features of the generator of the device of the invention.

FIG. 2 illustrates the main components of the generator 10.

The generator 10 includes a unit 24 for collecting and processing data produced by the cardiac activity sensor (lead 16) and the activity sensor (G sensor 22) to determine and calculate various parameters that will be described below. These parameters control a VNS generator 26 delivering electrical pulses to the lead 12. The energy (current or voltage stimulation by pulses of controlled width), the burst configuration, the repetition frequency, the duty cycle, etc., of the pulses are determined by the unit 24.

The generator 10 also includes a data memory 28 for recording the data calculated by the unit 24 in order to form histograms and comparative series of data over the long term.

The generator 10 is also provided with a communication interface 30, allowing the generator 10 to exchange by telemetry data with external devices such as a programmer 32 and/or a home monitoring device 34. This allows for remote transmission of information stored in memory 28 to a remote site for daily monitoring of the patient from this remote site.

The method by which the signals collected by the sensors are processed within the generator 10 according to various teachings of the invention will now be described in detail.

According to one embodiment, this therapy consists of three phases, namely:

a patient monitoring phase (the details of which will be given in reference to the flowchart in FIG. 12) for producing series of data of reference heart rate $HR_{ref}$ and of intrinsic heart rate $HR_{int}$, memorizing these series in the long term, establishing histograms and extracting these indicators of the patient's condition over the long term;

a phase of adjustment of the parameters of the VNS stimulation (the details of which will be given in reference to the flowchart in FIG. 13) according to the status indicators obtained during the previous phase; and a possible phase of delivering of alerts (the details of which will be given in reference to the flowchart in FIG. 14), intended to warn the doctor in case of worsening of the patient's condition.

First Phase: Monitoring and Evaluation of the Patient's Condition

The period of supervision or monitoring is the period during which the data is collected, processed and analyzed to then estimate the change in the long term of the patient's condition. This period may be fixed or variable. In this example, the monitoring period is set at 24 hours but may be set for any amount of time (one week, one month, etc.) or vary according to the condition of the patient (e.g., a more critical or less critical condition).

During this monitoring period, two parameters are measured continuously, namely the heart rate (HR) and the patient's activity level.

If the activity level is measured by an acceleration sensor (G sensor), the signal is filtered to keep only a bandwidth of typically between 0.6 and 6 Hz to remove the static component according to the patient position and experienced external vibrations, especially when the patient takes a mode of transport. The filtered signal is then averaged, e.g. over a period of Y=6 s, resulting in a sample $G_{mean}$ of average activity level, issued every Y seconds.

Figure 3:
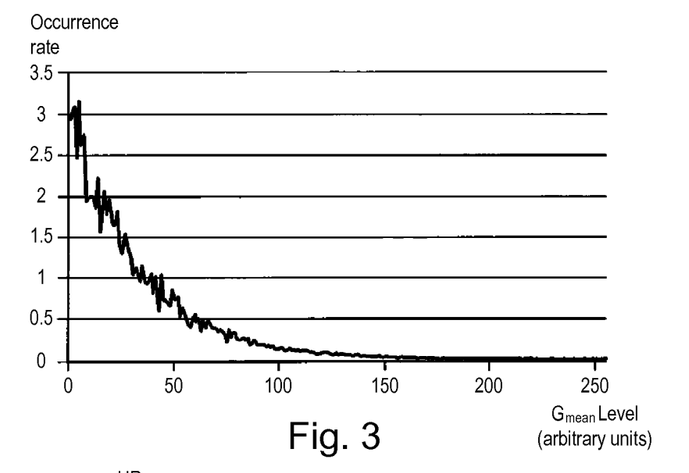
FIG. 3 is a histogram, established on 24 hours, of the patient activity mean values measured by an accelerometric sensor.

The distribution of these $G_{mean}$ activity values over a period of e.g. 24 hours is illustrated in FIG. 3.

According to one exemplary embodiment, this $G_{mean}$ activity level value is used to determine a value of the reference heart rate $HR_{ref}$ corresponding to the expected heart rate of the patient if he/she was healthy, for his/her activity level.

This reference heart rate $HR_{ref}$ is calculated every X cardiac cycles, typically X=4 cycles, depending on the last sample delivered by the activity sensor.

The following linear relationship is applied for this purpose, which defines the transfer function of the G sensor:

$$Fg = \text{Basic\_rate} + (\text{G\_sample} + \text{G\_low\_point})\frac{\text{Max\_rate} - \text{Basic\_rate}}{\text{G\_high\_point} - \text{G\_low\_point}}$$

Fg being a heart rate corresponding to a target value $HR_{target}$, G_sample being the last signal sample value issued by the G sensor, and Basic_rate, G_low_point, G_high_point and Max_rate being custom constants, parameterized by the physician based on the physical activity of each patient; alternatively, these values can be set to an arbitrary average value, as long as they do not change over time.

Figure 4:
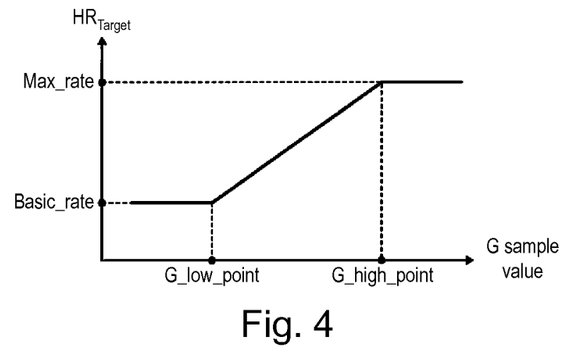
FIG. 4 shows the transfer function for obtaining a target value of heart rate based on the sample value of the activity signal G.

FIG. 4 illustrates the transfer function $HR_{target}=f$(G_sample) corresponding to the relationship given above.

Figure 5:
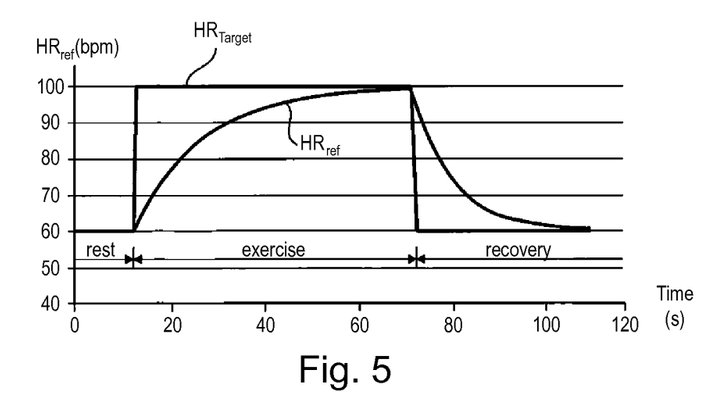
FIG. 5 shows the transfer function for, with application of a time constant, getting the reference heart rate from the target heart rate.

$HR_{target}$, which is calculated every four cardiac cycles, is raw data with rapid changes, for example during rest/activity/recovery cycles, as shown in FIG. 5.

Additional filtering is needed to reproduce the natural smoothing of the changes in heart rate between rest and activity, by application of a time constant according to a technique described for example in EP 0657187 A1 (Sorin CRM S.A.S). The resulting value is the reference heartbeat $HR_{ref}$ that will be used later in the data processing.

In FIG. 5, the patient is initially in a resting phase, the two $HR_{target}$ and $HR_{ref}$ values being at a value corresponding to the patient's baseline rhythm. During the exercise phase that follows, heart rate $HR_{target}$ immediately goes to 100 bpm, while reference heart rate $HR_{ref}$ increases slowly until reaching the $HR_{target}$ value after about sixty seconds. When the exercise is completed, $HR_{target}$ immediately falls to 60 bpm during the recovery phase, while the reference heart rate $HR_{ref}$ slowly decreases to this value after about thirty seconds.

Figure 6:
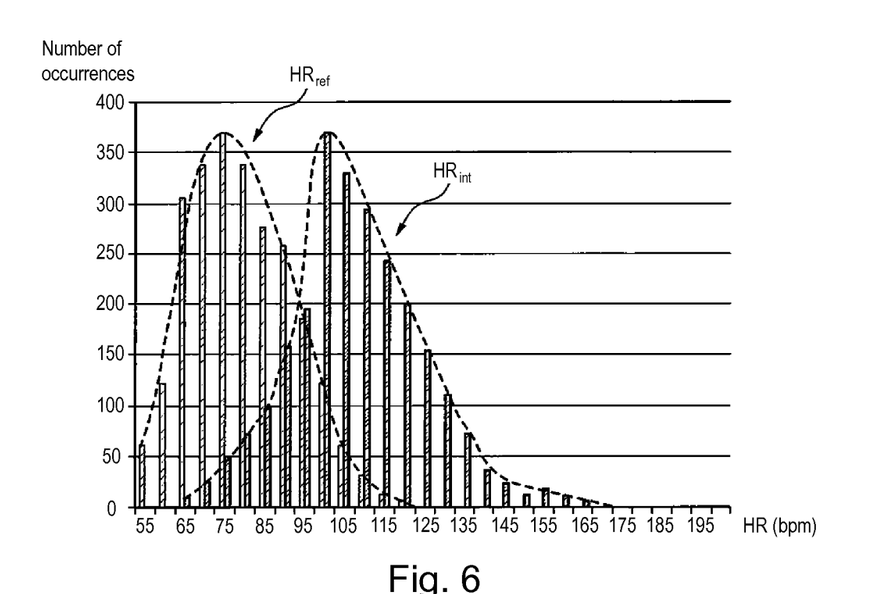
FIG. 6 shows the comparison between two histograms obtained respectively from the measured intrinsic heart rate and the reference heart rate determined by the calculation.

A histogram of $HR_{ref}$ values thus calculated is established on the duration of the monitoring period. FIG. 6 shows the histogram.

Meanwhile, during the same monitoring period, the patient's intrinsic heart rate is measured, and a second histogram is constructed from the values $HR_{int}$ thus obtained.

The intrinsic heart rate is the "normal-normal" rate determined from the detected RR intervals, excluding abnormal cycles (including extrasystoles) or insignificant cycles (especially noise cycles). Reference may be made for this definition to "Heart Rate Variability. Standards of Measurement, Physiological Interpretation, and Clinical use. Task Force of the European Society of Cardiology and the North American Society of Pacing and Electrophysiology." Eur Heart J, 17 (3): 354-381 (1996).

Note that both $HR_{ref}$ and $HR_{int}$ histograms include the same basic statistical parameters, namely bins of the same duration, typically 5 bpm, and sampling at a same frequency, typically every four cardiac cycles.

At the end of each monitoring period (typically daily), each of the two histograms $HR_{ref}$ and $HR_{int}$ thus formed is analyzed on the basis of one or more parameters characterizing the histogram (e.g. maximum value reached, average value, median and/or area included under the curve, or any other statistical relationship between the two histograms). A representative daily index is then stored for $HR_{ref}$ and for $HR_{int}$.

Figure 12:
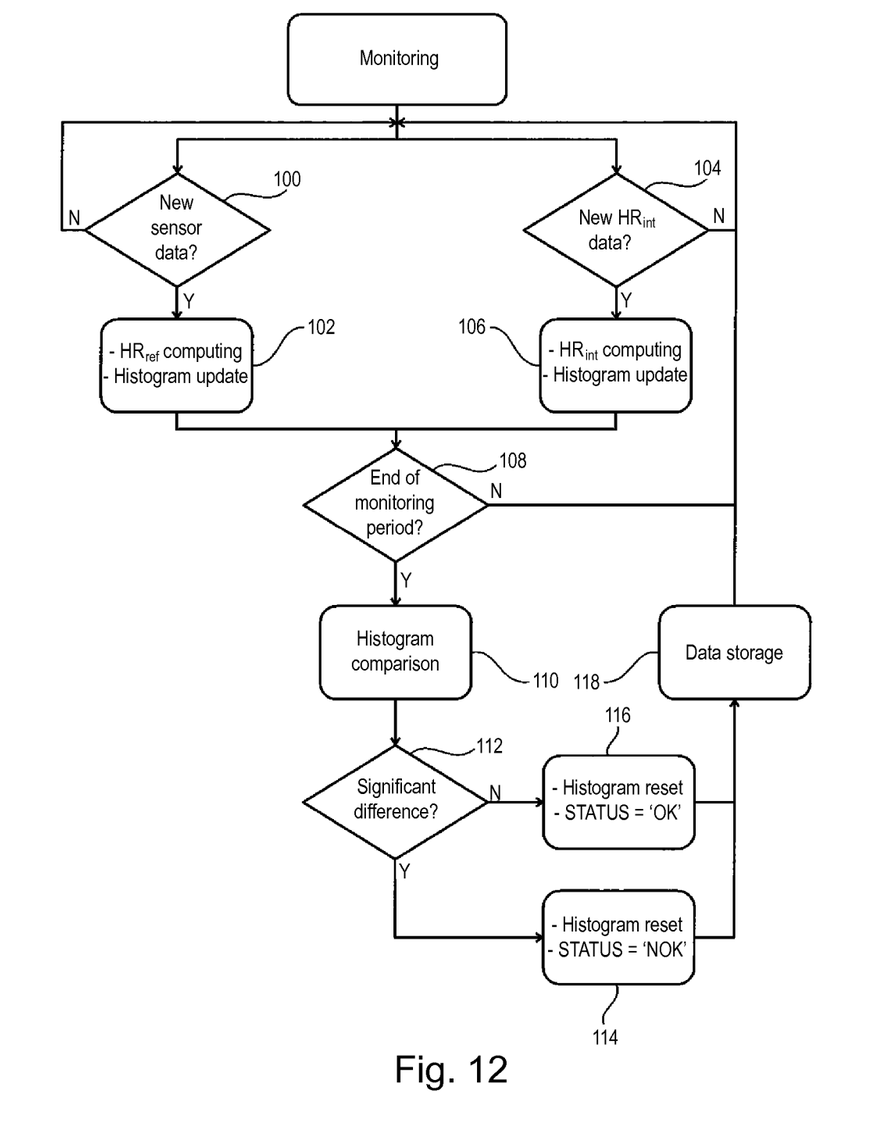
FIG. 12 is a flowchart showing the sequence of steps of a first monitoring phase of a technique of the invention.

FIG. 12 shows in flowchart form the various successive steps of this monitoring phase.

When the G sensor provides new data (block 100), the reference heart rate $HR_{ref}$ is calculated as shown above (block 102) and the corresponding histogram is updated.

Meanwhile, when new heart rate data to calculate the intrinsic rhythm is available (block 104), the $HR_{int}$ value is recalculated and the corresponding histogram is updated (block 106).

At the end of the monitoring period (block 108) the two histograms are compared (block 110), depending on the different parameters that can characterize each histogram (average value, median value, maximum value, area under the curve, statistical test, etc.). If a significant difference is detected (e.g., a difference value above a threshold value) (block 112), a STATE flag is set to 'OK' or 'NOK' and the histograms are reset (blocks 114, 116). Data for $HR_{ref}$ and $HR_{int}$ are then stored (block 118) for further evaluation.

Second Phase: Analysis of the Evolution of the Patient's Condition

The indexes obtained daily for $HR_{ref}$ and $HR_{int}$ values, which reflect the condition of the patient at a given day, are compared in order to assess their relative change in the long term.

Figure 7:
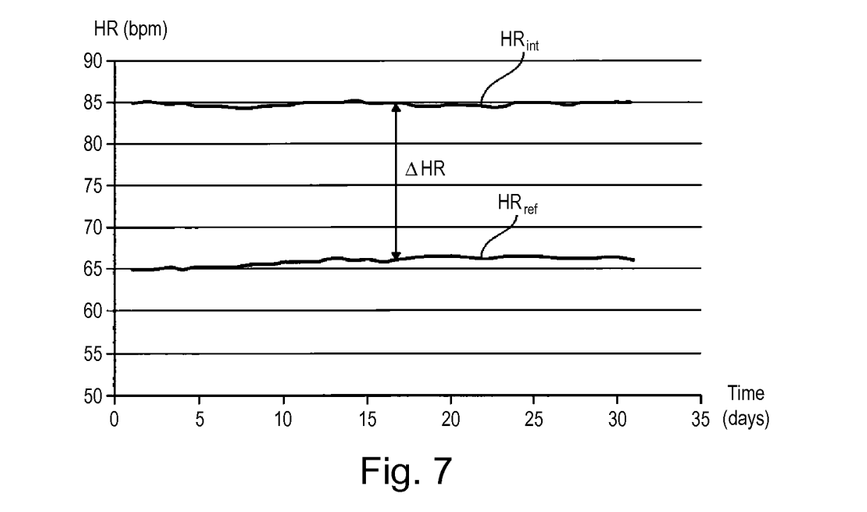
FIG. 7 shows the evolution in the long term of the intrinsic and reference heart rates in the case of a patient whose condition does not vary significantly.

FIG. 7 illustrates an example of evolution of these indexes over approximately one month. It is noted that, in this case, the gap $\Delta HR$ between the two curves $HR_{ref}$ and $HR_{int}$ remains substantially constant, indicating that the patient's condition remains stationary.

Figure 8:
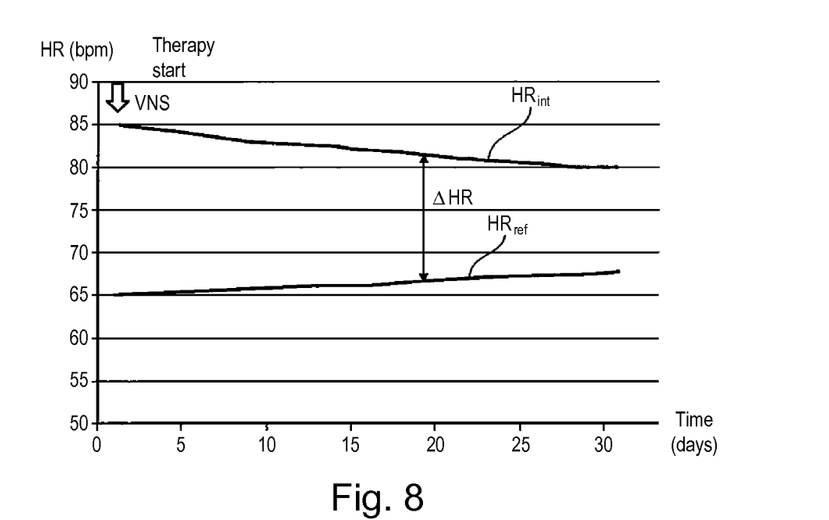
FIG. 8 is homologous to FIG. 7, for a patient whose condition is improving due to the application of VNS therapy.

FIG. 8 is similar to FIG. 7, after insertion of a VNS therapy continued throughout the duration of the study.

VNS therapy should normally increase $HR_{ref}$ (under the effect of the patient's improvement to achieve physical activity) and decrease $HR_{int}$, which is what is seen on the curves in FIG. 8.

Therefore, a significant improvement in the patient's condition can be diagnosed as the result of applied VNS therapy.

Figure 9:
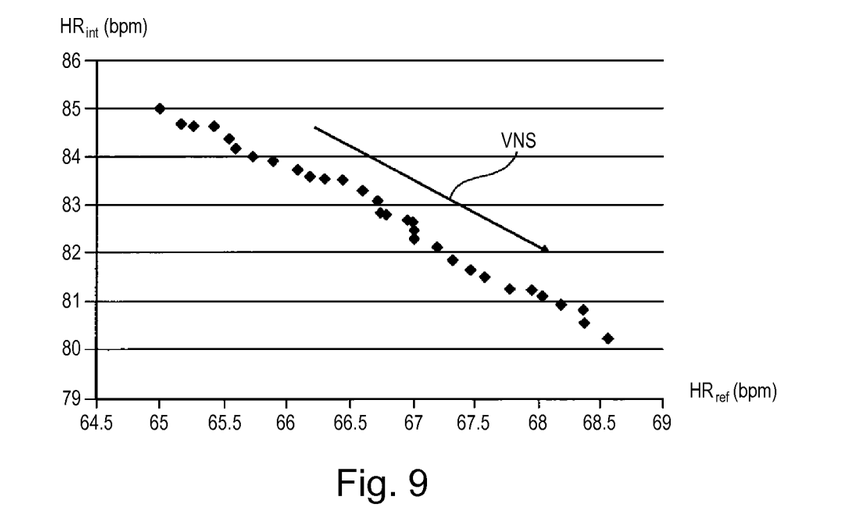
FIG. 9 is a representation, in coordinates independent of time, of the two intrinsic heart rate and reference heart rate parameters whose evolution is shown in FIG. 8.

In a functional representation as illustrated FIG. 9 (with $HR_{int}$ versus $HR_{ref}$), it can be seen that the two parameters are associated approximately linearly with a negative slope reflecting the favorable evolution of the patient's condition under the effect of the applied therapy ("VNS" arrow).

Figure 10:
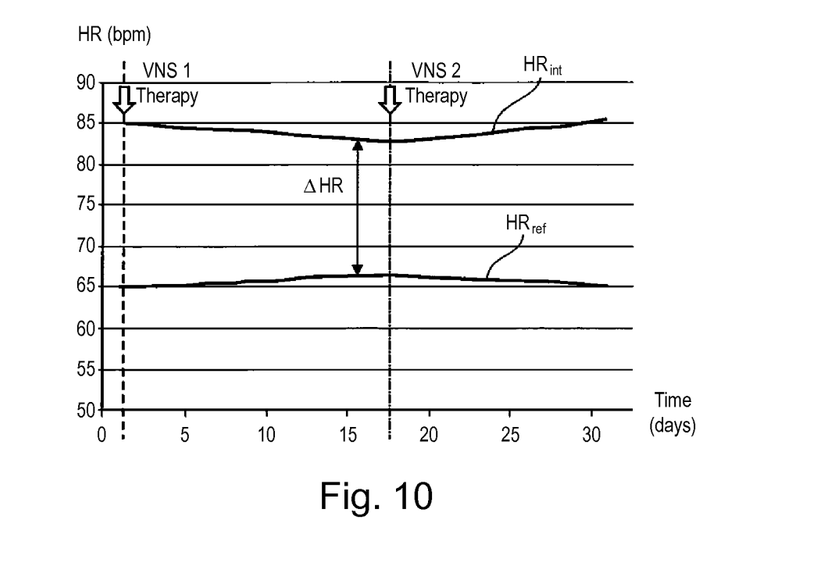
FIGS. 10 and 11 are homologous to FIGS. 8 and 9, in the case wherein the initially applied VNS therapy is changed during the period.
Figure 11:
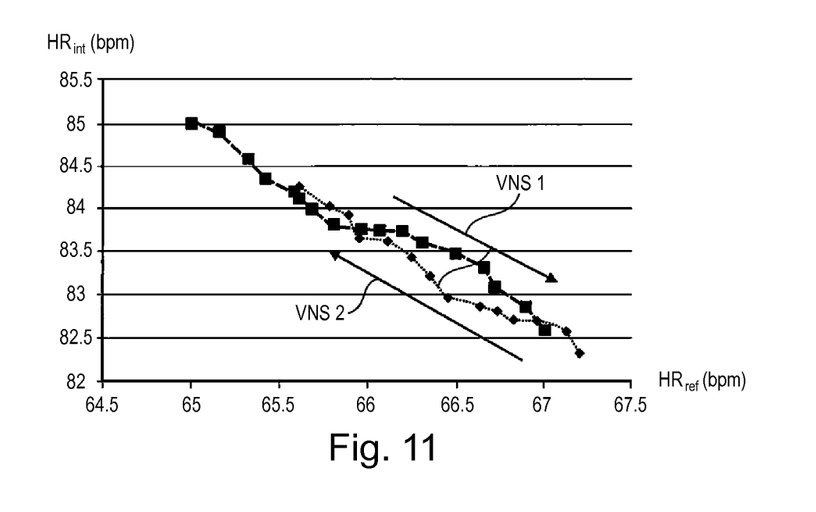

FIGS. 10 and 11 are homologous to FIGS. 8 and 9, in a situation wherein the VNS therapy initially applied (VNS1, for example stimulation by bursts of four pulses of 3 mA, 0.24 ms width, with a 1/1 duty cycle and a sequencing of 10"/30") has been changed after a fortnight (VNS2, for example stimulation by bursts of 2 pulses of 2 mA, 0.24 ms width, with a 1/1 duty cycle and a sequencing of 10"/30"), for example with increase/decrease of the stimulation energy, change in frequency and/or content of the pulse bursts, of their duty cycle, etc. Note that 10"/30" sequencing refers to a repeated pattern of 10 seconds of active VNS stimulation followed by 30 seconds of no stimulation.

It is then found that, after having converged (improvement of the patient's condition), the two curves come to deviate, this reflecting degradation of the patient's condition after the therapy has been modified from VNS1 and VNS2.

On the functional representation of FIG. 11, the squares illustrate the successive values recorded during the first period, while the diamonds illustrate those recorded during the second period. There is a reversal of direction (between the "VNS1" arrow and the "VNS2" arrow), reflecting in the second period a deterioration of the condition of the patient because of the new therapy.

In response, the parameters of VNS therapy may be adjusted so as to return to a configuration improving the patient's condition.

This re-setting may be performed periodically, for example weekly, until the gap between the two $HR_{ref}$ and $HR_{int}$ curves decreases below a predefined threshold ($HR_{ref}$, which is a calculated value based on patient activity, representing the ideal towards which $HR_{int}$ must converge).

The periodicity of the adjustment of VNS parameters can be the same as the monitoring period (e.g. daily), or much longer than the monitoring period (for example weekly) to adjust VNS therapy more slowly.

Figure 13:
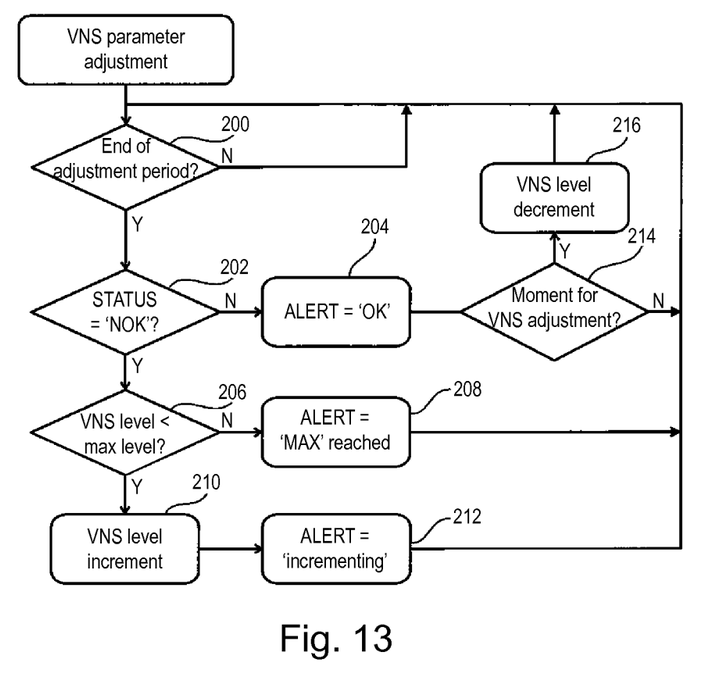
FIG. 13 is a flowchart showing the sequence of steps of a second phase of VNS therapy adjustment, of a technique of the invention.

FIG. 13 shows in flowchart form the steps of this phase of adjustment of VNS parameters.

At the end of the predetermined duration of the adjustment phase (block 200), the indicator STATUS is tested (block 202). If this is the value 'OK', an ALERT parameter is set to 'OK', meaning that the patient is compliant and does not trigger any alert.

In this case, the VNS therapy should be reassessed at regular intervals (block 214). If that time is reached, for example after seven consecutive 'OK' days, the level of VNS stimulation is reduced (block 216). For example, the number of pulses of each VNS burst is reduced by one, and if a lower limit is reached, for example two pulses per burst, then the current supplied is decreased by a step (typically 0.5 mA).

If the STATUS indicator is 'NOK', then the device examines whether the level of VNS stimulation is at its maximum (block 206). If so, the ALERT parameter is set to 'MAXIMUM REACHED', to signify that, although the indicator's status is unsatisfactory, the VNS stimulation has reached the maximum level it was possible to issue (block 208). Otherwise, the level of VNS stimulation is increased (block 210) and the ALERT parameter is set to 'INCREMENT' (block 212) to indicate that it was necessary to apply to the patient a higher VNS therapy. For example, the number of VNS pulses of each burst is increased by one unit, and if an upper limit is reached, for example, four pulses per burst, then the delivered current is increased one step (typically 0.5 mA).

However, to decrease or increase the effect on heart rate, any other parameter can be modulated to achieve the desired effect (pulse frequency, QRS-VNS burst delay, etc.).

Third Phase: Management of the Alerts

If $HR_{ref}$ and $HR_{int}$ curves come to diverge (as in the second period illustrated FIG. 10), it may be desirable to warn the physician without waiting for the follow-up visit, for example by generating an alert and by transmitting it to a remote site via a home monitoring system.

Figure 14:
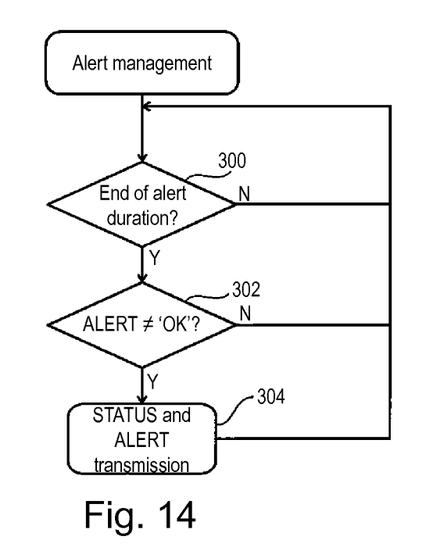
FIG. 14 is a flowchart showing the sequence of steps of a third phase, consisting of alert management, of a technique of the invention.

FIG. 14 illustrates, in flowchart form, the different steps of the third phase of alert management.

At the end of the predetermined time of alert management (block 300), for example daily, the ALERT flag is examined (block 302). If it is not at the 'OK' value, then the values of the STATUS and ALERT indicators are remotely transmitted (block 304) for analysis and possible action by the practitioner, typically using a home monitoring system connected to a remote site.

What is claimed is:

1. An active implantable medical device for the treatment of heart failure by stimulation of a vagus nerve (VNS) or one of its branches, comprising:
   a VNS pulse generator and an electrode adapted to be placed on or close to the vagus nerve of a patient;
   an activity sensor capable of delivering successive values of the patient's current activity level; and
   a processor configured to:
   collect the electrical activity of the heart, the electrical activity used to determine successive values of a current intrinsic heart rate of the patient;
   calculate successive values of a reference heart rate based on the respective successive values of the patient's current activity level, wherein calculating the successive values of the reference heart rate comprises filtering the values of the calculated reference heart rate, by application of a time constant;
   construct a first histogram from the reference heart rate depending on the respective values of the patient's current activity level delivered by the activity sensor, over a predefined monitoring period;
   construct a second histogram, distinct from the first histogram, from the intrinsic heart rate values over the predefined monitoring period; and
   derive an index representative of the patient's condition at the end of the predefined monitoring period, by comparing the first and second histograms.

2. The device of claim 1, wherein the comparison of the first and second histograms comprises:
   calculating, for each of the first and second histograms, at least one histogram parameter, and
   comparing the at least one histogram parameter of the first and second histograms.

3. The device of claim 2, wherein the at least one histogram parameter is at least one of a maximum value of the histogram, a mean of the histogram values, a median of histogram values, an area under the envelope curve of the histogram, or a combination thereof.

4. The device of claim 1, wherein calculating the reference heart rate comprises applying the following relationship:

$$Fg = \text{Basic\_rate} + (\text{G\_sample} + \text{G\_low\_point}) \frac{\text{Max\_rate} - \text{Basic\_rate}}{\text{G\_high\_point} - \text{G\_low\_point}}$$

where Fg is the value of the reference heart rate, G_sample is the value of the patient's current activity level issued by the activity sensor, and Basic_rate, Max_rate, G_high_point and G_low_point are predetermined constants.

5. The device of claim 1, wherein the processor is further configured to evaluate changes in the index representative of the patient's condition over a plurality of successive monitoring periods.

6. The device of claim 5, wherein the processor is further configured to modify at least one operating parameter of the VNS pulse generator based on whether the changes in the index representative of the patient's condition over the plurality of successive monitoring periods meet one or more predetermined criteria.

7. The device of claim 5, wherein the processor is further configured to trigger an alert based on whether the changes in the index representative of the patient's condition over said plurality of successive monitoring periods meet one or more predetermined criteria.

8. A method for the treatment of heart failure by stimulation of a vagus nerve (VNS) or one of its branches, comprising:
   collecting values of a patent's activity level;
   collecting an electrical activity of a heart, the electrical activity comprising successive values of the intrinsic heart rate of the patient;
   calculating successive values of a reference heart rate based on successive values of the patient's activity level, wherein calculating the successive values of the reference heart rate comprises filtering the values of the calculated heart rate, by application of a time constant;
   constructing a first histogram from the reference heart rate depending on the successive values of the patient's activity level, over a predefined monitoring period;
   constructing a second histogram, distinct from the first histogram, from the intrinsic heart rate values over the predefined monitoring period; and
   deriving an index representative of the patient's condition at the end of the predefined monitoring period, by comparing the first and second histograms.

9. The method of claim 8, wherein the comparison of the first and second histograms comprises:
   calculating, for each of the first and second histograms, at least one histogram parameter, and
   comparing the at least one histogram parameter of the first and second histograms.

10. The method of claim 9, wherein the at least one histogram parameter is a parameter of a group including a maximum value of the histogram, a mean of the histogram values, a median of histogram values, an area under an envelope curve of the histogram, and combinations of the preceding.

11. The method of claim 8, wherein calculating the reference heart rate comprises applying the following relationship:

$$Fg = \text{Basic\_rate} + (\text{G\_sample} + \text{G\_low\_point}) \frac{\text{Max\_rate} - \text{Basic\_rate}}{\text{G\_high\_point} - \text{G\_low\_point}}$$

where Fg is the value of the reference heart rate, G_sample is the value of the patient's activity level, and Basic_rate, Max_rate, G_high_point and G_low_point are predetermined constants.

12. The method of claim 8, further comprising:
evaluating the changes in the index representative of the patient's condition over a plurality of successive monitoring periods.

13. The method of claim 12, further comprising:
modifying at least one operating parameter of a VNS pulse generator based on whether the changes in the index representative of the patient's condition over the plurality of successive monitoring periods meet one or more predetermined criteria;
wherein the VNS pulse generator is placed on or close to the vagus nerve.

14. The method of claim 12, further comprising:
triggering an alert based on whether the changes in the index representative of the patient's condition over said plurality of successive monitoring periods meet one or more predetermined criteria.

15. The method of claim 8, wherein an activity sensor is configured to deliver successive values of the patient's activity level.

16. A method for the adjustment of an operating parameter of a vagus nerve stimulation (VNS) pulse generator, the VNS pulse generator configured to provide treatment of heart failure of a patient, comprising:
deriving an index representative of the patient's condition over a predefined monitoring period;
evaluating the changes in the index representative of the patient's condition over a plurality of successive monitoring periods;
determining whether the changes in the index meet one or more predefined criteria;
setting an alert parameter to an 'OK' value if the one or more predetermined criteria are not met;
reassessing the changes in the index at regular intervals; and
reducing the level of stimulation provided by the VNS pulse generator if the number of intervals for which the one or more predetermined criteria are not met reaches a threshold value.

17. The method of claim 16, further comprising:
setting an alert parameter to a 'NOK' value if one or more of the predetermined criteria are met;
determining if the level of stimulation provided by the VNS pulse generator is at a maximum value;
generating an alert that the level of stimulation is at a maximum value if the level of stimulation is at the maximum value; and
increasing the level of stimulation provided by the VNS pulse generator and generating an alert to the increase of the level of stimulation if the level of stimulation is not at the maximum value.

* * * * *